United States Patent [19]
Burwell et al.

[11] Patent Number: 5,824,880
[45] Date of Patent: Oct. 20, 1998

[54] AUTOMATED DROP-WEIGHT IMPACT TESTING

[75] Inventors: Fred J. Burwell, Bartlesville; Ronald D. Jones, deceased, late of Bartlesville, by Catherine Z. Jones, Joseph B. Cross, executors; Wayne A. Millard, Bartlesville; Dennis C. Sprague, Bartlesville; Herbert R. Pinnick, Jr., Bartlesville; George L. Dorsey, Bartlesville, all of Okla.

[73] Assignee: Phillips Petroleum Company, Bartlesville, Okla.

[21] Appl. No.: 866,005

[22] Filed: May 30, 1997

[51] Int. Cl.$^6$ .................................................. G01N 3/00
[52] U.S. Cl. .................................... 73/12.06; 73/12.07
[58] Field of Search .................... 73/12.02, 12.04, 73/12.01, 12.06, 12.07, 12.09, 12.13; 364/551.01, 556

[56] References Cited

U.S. PATENT DOCUMENTS

| | | |
|---|---|---|
| 4,023,396 | 5/1977 | Yakshin et al. ................... 73/12.04 |
| 4,313,337 | 2/1982 | Myint ................................ 73/12.13 |
| 4,344,142 | 8/1982 | Diehr, II et al. ..................... 364/473 |
| 4,514,796 | 4/1985 | Saulters et al. ..................... 364/142 |
| 5,490,411 | 2/1996 | Hogan ............................... 73/12.13 |
| 5,497,649 | 3/1996 | Ambur et al. ...................... 73/12.06 |
| 5,540,078 | 7/1996 | Ambur et al. ...................... 73/12.13 |
| 5,568,593 | 10/1996 | Demarest et al. ................... 395/82 |

*Primary Examiner*—Max H. Noori
*Attorney, Agent, or Firm*—George E. Bogatie

[57] ABSTRACT

A test fixture of the type that requires repeated manual lifting of weights in a drop-tube for performing an ASTM drop weight test, is provided with a computer automated pneumatically powered lift mechanism. The lift mechanism for the weights responds to a series of computer generated signals that are applied to a set of electropneumatic actuators for driving pistons to lift and drop the weight. Associated with the lift mechanism is a set opto-interrupter devices that generate a position signal representative of the position of the weight to be dropped as it ascends in the drop tube. In use the computer is provided with a desired drop height and essentially continuously compares the position signal with the desired drop height and releases the weight in the drop tube to impact a sample material when the position signal equals the desired drop height.

6 Claims, 6 Drawing Sheets

| Operator ID: | RB | | | | | | | | | Date: | 05/27/1997 | | | | | | | | | | | Mean Failure Height: | 21.3 | inches |
|---|---|---|---|---|---|---|---|---|---|---|---|---|---|---|---|---|---|---|---|---|---|---|---|---|
| Sample ID: | 97-PP00763 | | | | | | | | | Material: | PP | | | | | | | | | | | Drop Weight | 8 | lbs |
| Temperature: | 23°c | | | | | | | | | Thickness: | 0.122 inches | | | | | | | | | | | Gardner Impact | 170.22 | inch-lbs |
| Humidity: | 50 % | | | | | | | | | Test Type: | GC | | | | | | | | | | | | | |
| Height | 1 | 2 | 3 | 4 | 5 | 6 | 7 | 8 | 9 | 10 | 11 | 12 | 13 | 14 | 15 | 16 | 17 | 18 | 19 | 20 | $n_x$ | $n_o$ | i | in$_i$ |
| 23 | X | | | | | | | | | | | | | | | | | | | | 2 | | 2 | 4 |
| 22 | O | O | | X | X | | X | | X | X | | | X | | | | | X | | | 4 | 2 | 2 | 3 |
| 21 | | | O | | | O | | O | O | | X | | O | X | | X | X | | | | 5 | 3 | 1 | 0 |
| 20 | | | | | | | | | | | | O | | | O | | O | O | O | | 4 | 4 | 0 | 0 |
| | | | | | | | | | | | | | | | | | | | | TOTAL | 11 | 9 | | 7 |

*FIG. 5*

AUTOMATED DROP-WEIGHT IMPACT TESTING

The present invention relates generally to drop-weight impact testing of materials that fail by cracking or shattering under sufficient impact stress delivered by a single blow, and more specifically to computer controlled power lifting conveyors that automate weight lifting for a standard impact testing machine.

BACKGROUND OF THE INVENTION

Impact resistance is one of the most important end-use stresses to which plastic parts are subjected. In the case of plastic design, impact failure is related to part geometry, impact variables, and material construction. Therefore, impact tests are useful to rank materials and to explore quantitatively the effect of pertinent variables such as temperature, speed and notching. All impact test data require careful interpretation to end uses because all are subject to specimen interaction with the test method. This is because impact performance can be profoundly affected by ordinary fabrication variables such as thermal history, flow patterns, drawdown ratios and orientation of the polymer or filler. Accordingly, the design of impact resistant parts must rely heavily on testing of materials under actual or simulated conditions of end use.

A test less prejudice to the above-mentioned interactions that is widely used in the plastic industry for general ranking of plastic material is the drop-weight test. The drop-weight test according to ASTM D-3029 is by far the best test for general material characterization. This is primarily because it is set up to measure the energy to initiate a fracture and is simple in construction and easy to operate. Speed of loading can be independently varied easily over a fairly wide range, and testing at cold temperatures is readily done. Energy measurement is simple and does not require instrumentation. In the drop-weight test, a specimen, usually a disc, is supported horizontally over a relatively small diameter hole in a steel base plate. A weight is dropped from a measured height impacting at the center of the specimen by means of a projecting striker having a hemispherical shape (i.e., tup). In a constant height test, a sequence of drops is made with increasing weight (constant speed at impact) on successive fresh specimens until a failure is visibly observed. By a statistical method which minimizes the number of specimens required, a mean failure rate is calculated. From this failure rate and the drop height a mean failure energy is calculated and reported. This test sequence can then be repeated at higher drop heights to test systematically for the effect of loading speed. The ASTM specification also makes provisions for calculating standard deviation from which an estimate of the threshold failure energy can be made. The scatter of the data may also be useful for indicating the kind of fabrication and material variables that are sources of impact failures.

The limitations of the drop-weight test are primarily that it requires a large number of test specimens and a lengthy testing time for each determination. While the drop-weight test is not suitable for flexible materials or high impact materials that do not fail by cracking or shattering, it is the best impact test available for general description of materials since it tends to rank materials according to their performance in average end-use situations.

A Gardner impact test is an ASTM standard drop-weight test widely used to gauge the impact strength of plastics. For the Gardner impact test, a test fixture is used which includes a base plate, a round-nosed steel impact weight called a dart that typically ranges in weight from one-fourth to twelve pounds, a vertically mounted slotted forty-two inch drop-tube having inch-pound graduations, in which the dart is manually lifted up and dropped. Impact resistance is determined by subjecting either side of a sample specimen to an impact of up to 320 inch-pounds, depending upon the weight dropped. The sample specimen is placed over a one-half inch diameter hole in the base plate. The dart of selected weight is raised by lifting an attached pin until the pin coincides with the desired inch-pound graduation mark on the slotted tube, and then the dart is released to fall through the drop tube and impact the test specimen. The sample specimen is examined for cracking or failure after each impact. Any small cracking damage can most easily be recognized by observing cracking on the reverse side of the specimen. This detection is made relatively easy by inking the reverse side of the specimen and then wiping it clean after the impact, such that the ink clearly identifies any local cracking due to the impact.

The disadvantage of the Gardner test, in addition to requiring a large number of test specimens, is that the darts can only be lifted manually using a short metal pin that extends through the slot in the slotted drop tube. Lifting a twelve-pound dart hundreds of times per day to heights of up to thirty-eight inches (usually above a tabletop) is both tiresome and potentially hazardous. Another disadvantage of the Gardner test is that resulting test data can only be recorded manually.

Accordingly, it is an object of this invention to provide a powered lift mechanism for lifting and release weights required for Gardner impact testing.

Another object of this invention is to simplify recording of test data resulting from Gardner impact testing.

A more specific object is to provide a pneumatic powered lift mechanism for use with the Gardner test fixture that can contact the darts' pin and lift the dart to the desired drop height.

A still more specific object it to detect the height of the dart in the slotted tube of the Gardner fixture by activating and detecting the state of a series of opto interrupts as the dart ascends in the drop-tube.

Still, another object is to automatically recycle the dart engagement mechanism down the test fixture to its initial position for recontacting the dart for repeating the drop-weight test.

SUMMARY OF THE INVENTION

According to this invention the foregoing as well as other objects are attained by an apparatus and method for automating the weight lifting required to operate a well-known test fixture for drop-weight testing of materials that fail by cracking or shattering under a single blow of sufficient impact stress. This invention provides apparatus including a pneumatic power lift mechanism for use with the drop-weight test fixture, where the lift mechanism is responsive to a series of electronic signals that sequence operation of a set of pneumatic valves for both lifting and releasing of a dart from a desired height in the test fixture. The lift mechanism also implements generation of a digital type electronic signal representative of the position of the dart as it ascends in the test fixture.

In another aspect, the method of the invention for drop-weight testing is aided by a computer and involves, providing drop-weight data to a computer connected to a power lift mechanism, which data includes at least the weight of the dart to be dropped and the height of the drop; placing a sample of material over a hole in the base plate of a drop-weight test fixture; placing the selected weight in a drop-tube of the test fixture; using the computer to generate a signal to activate the power lift mechanism, thereby lifting the weight and releasing it from the desired height; recycling the power lift mechanism to it's starting position; examining the sample to determine results of the test, and using the computer for recording the test results.

The method and apparatus of the invention, using the power lift mechanism responsive to computer generated signals, thus tests a large number of samples in a relatively short period of time without manually lifting the impact weights. Further, the method of the invention simplifies recording of the drop-weight test data.

Other objects and advantages of the invention will become apparent from the following description of a preferred embodiment and the appended claims when taken in conjunction with the drawings.

BRIEF DESCRIPTION OF THE DRAWINGS

FIG. 5 is an example of a test report produced using the apparatus and method of the invention.

DESCRIPTION OF THE PREFERRED EMBODIMENT

This invention is applicable to a wide range of plastic materials which can be formed into shapes for many uses, and is particularly well suited for testing polyethylene and polypropylene copolymer compositions. The invention describes a drop-weight test apparatus and method in which a pneumatic power lift mechanism is used to repeatedly lift weights for drop-weight testing of plastic materials, thus relieving the test operator of a strenuous chore while reducing the time required for testing according to an ASTM specification.

Figure 1:
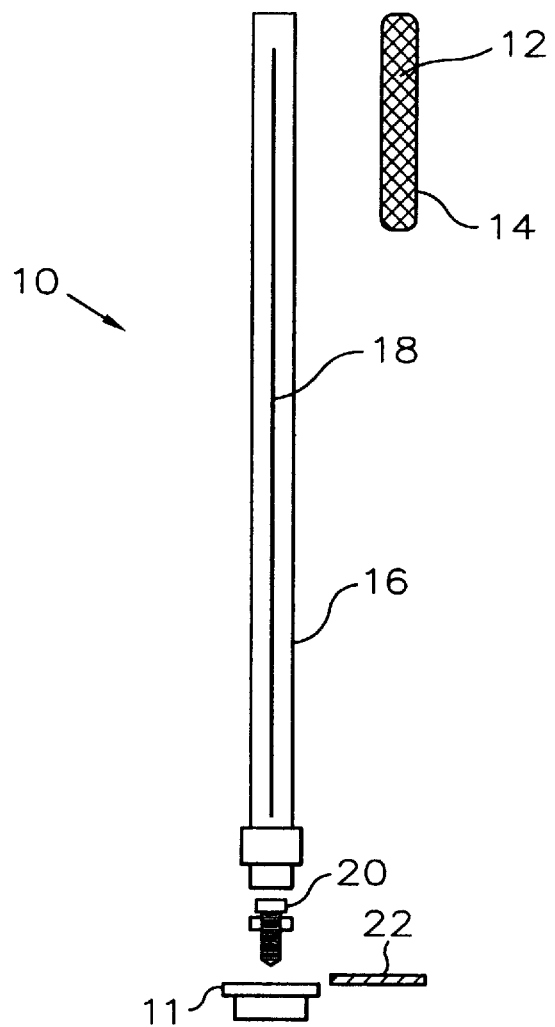
FIG. 1 is a schematic diagram illustrating essential components of a Gardner drop-weight impact test fixture.

In a preferred embodiment, the test fixture utilized is a commercially available test fixture for implementing a test according to ASTM procedures known as a Gardner impact test. Referring now to the drawings, wherein like elements are numbered alike in the several figures, FIG. 1 illustrates the Gardner test fixture generally shown at 10, which includes: a base plate 11 having a hole (not illustrated); several impact weights in the shape of a dart as illustrated at 12, and each dart having an outwardly extending lift pin 14; a drop-tube 16 having a slot 18 that is vertically mounted above the hole in the base plate 10 such that a dart 12 can be raised in the slotted drop-tube 16 by positioning the lifting pin through the slot 18 and using the lift pin 14 to manually lift the dart 12 to a desired height in the drop-tube 16. The dart is then released and allowed to fall through the drop-tube 16 to impact a dart hammer 20 resting on top of a polymer sample 22, which is pre-positioned over the hole in the base plate 11. Accordingly, when the dart 12 is dropped, the dart hammer 20 is driven partially into or through the polymer sample 22.

Figure 2:
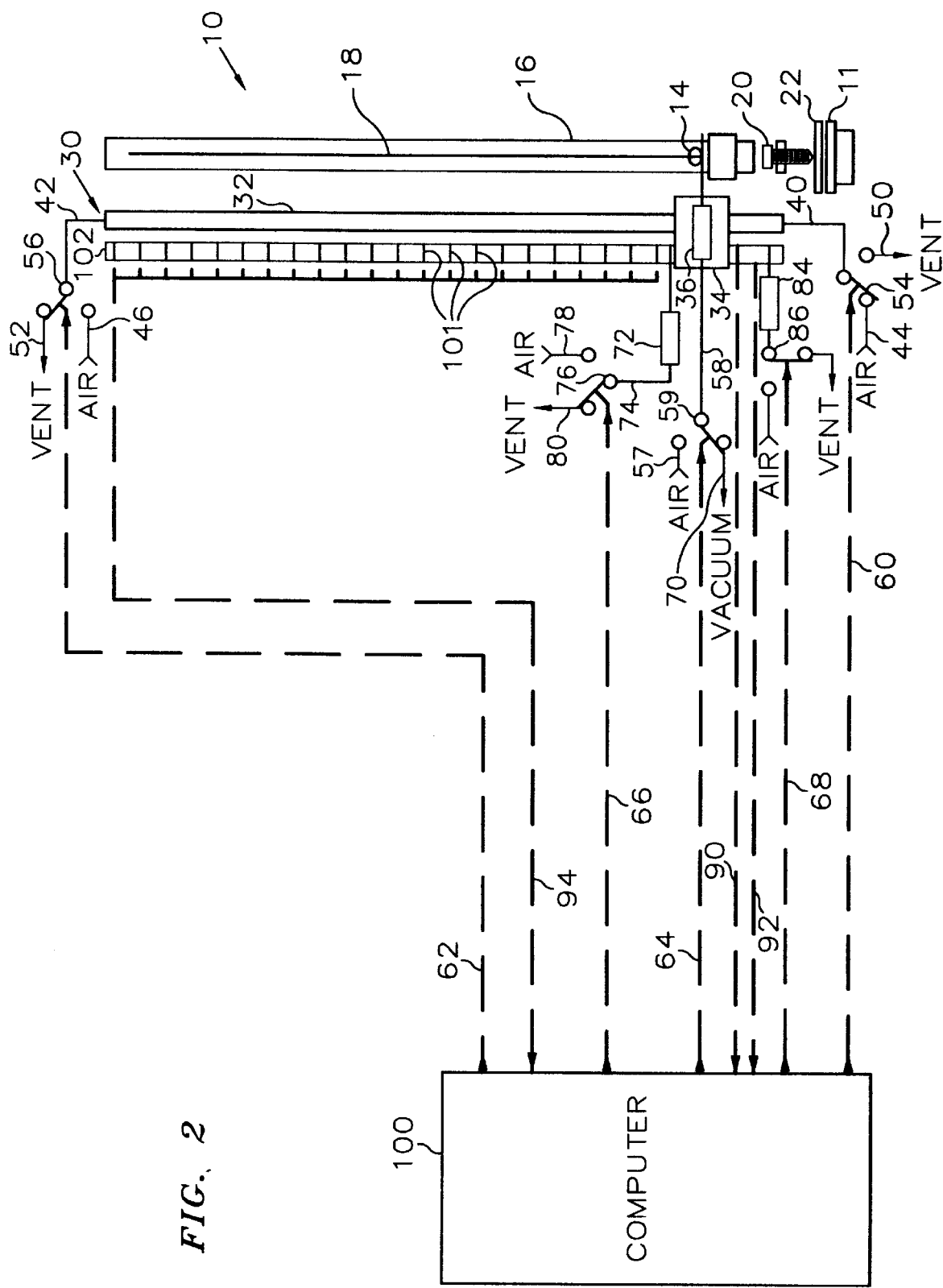
FIG. 2 is a simplified schematic diagram illustrating a computer controlled power lift mechanism for use with the Gardner drop-weight test fixture according to this invention.

The novel apparatus of the invention, which includes the power lift mechanism 30 with associated computer 100 and other control equipment, is shown in combination with the Gardner test fixture 10 in FIG. 2, where electronic signals associated with a computer 100 are shown as dashed lines. In addition to the computer 100, the novel apparatus includes a computer controlled pneumatic power lift mechanism, generally indicated at 30.

Several types of commercially available electropneumatic actuators that can respond to control signals from a digital computer to drive pistons are utilized in this invention to control operation of the pneumatic power lift mechanism 30. These include: (1) spring and diaphragm type pneumatic piston-cylinder construction where air supplied at an inlet can move the piston stem up to three inches in a desired direction, and then rapidly return the stem to its original position on release of air pressure. (2) pneumatic balanced (i.e. springless) diaphragm type pneumatic piston-cylinder construction for travel up to three inches, and (3) pressure balanced piston-cylinder construction having double acting air inlets (i.e., a working chamber at each end of the piston) which can controllably move the piston up to thirty-six inches. Such electropneumatic actuators are well known in the art, and are described at length in chapter 22 of Perry's "Chemical Engineers Handbook," 6th-Edition, 1984, McGraw-Hill, Inc.

As illustrated the power lift mechanism 30 requires five output signals 60, 62, 64, 66, and 68 to sequence operation of four electropneumatic piston cylinder actuators 32, 36, 72 and 84 for repeatedly lifting and dropping darts through the drop-cylinder 16. The actuators includes a lift piston 32, which is a double acting pressure balanced piston actuator, approximately the same length as the slotted drop-tube 16 and is positioned beside the slotted drop-tube 16 of the Gardner impact fixture 10. The lift piston 32 responds in a double acting manner to air pressure at inlet conduits 40 and 42. Through switch 54, inlet 40 can selectably be connected to an air pressure source through conduit 44 to move the piston 32 upwardly, or to a vent through conduit 50. The position of switch 54 is controlled by an electronic output signal 60 generated in computer 100. In a similar manner through switch 56, inlet 42 of lift piston 32 can selectably be connected to an air pressure source through conduit 46 to move the piston 32 downwardly, or to a vent through conduit 52. The position of switch 56 is controlled by computer output signal 62. In the switch positions for switches 54 and 56 shown in FIG. 2, air pressure is supplied to inlet conduit 40, and inlet conduit 46 being vented such that the lift piston 32 would move upwardly if it were not constrained by the start/home piston 72, as will be more fully explained hereinafter. Attached to the lift piston 32 is a small platform 34 that carries a drop piston 36. The drop piston 36, which is a pneumatic balanced diaphragm construction, is operated through switch 59 such that a vacuum source applied through conduit 70 extends the piston stem, and an air pressure applied through conduit 57 retracts the stem. The switch 59 is controlled responsive to signal 64. In the position shown in FIG. 2, the vacuum source supplied via conduit 70 extends the stem of drop piston 36 to contact the underside of pin 14 of a dart, which is contained in the drop-tube 16, so that the dart is raised with the lift platform.

A spring and diaphragm type pneumatic piston-cylinder construction is preferred for piston 72, which is used to prevent the double acting lift piston 32 from raising the dart until the desired start time. Accordingly, piston 72 is referred to herein as a home/start piston. An inlet conduit 74 for piston 72 is connected to switch 76 so that piston 72 can be supplied with air pressure via conduit 78 or vented via conduit 80. Switch 76 is controlled responsive to computer output signal 66. In the position of switch 76 shown in FIG. 2, the stem of piston 72 is extended so as to contact the top of platform 34, thus preventing the lift piston 32 from rising, even though air pressure supplied to piston 32 via switch 54 urges upward motion of piston 32. Another spring diaphragm type piston cylinder 84, referred to herein as a safety piston, is mounted near the bottom of the lift piston 32 to prevent the platform 34 from reaching the bottom of lift piston 32. The stem of piston 84 is extended when sample specimens are being loaded onto the base plate 11.

Figure 4:
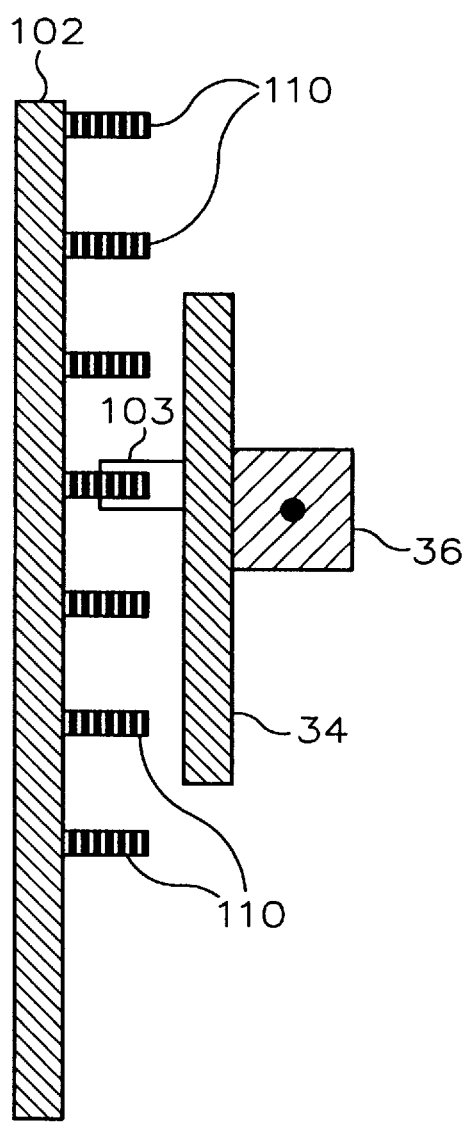
FIG. 4 is a partial side view illustrating the blade for triggering the opto-interrupt signals.

Also required for control of the pneumatic lift mechanism 30, as shown in FIG. 2, are three computer input signals 90, 92 and 94 that are generated by commercially available optoelectronic semiconductor interrupter modules mounted on a sensor post 102 positioned along a side of the lift piston 32. A series of opto interrupt modules 101 are spaced apart at one inch interval along the post 102, and are activated by a blade (not illustrated in FIG. 2) attached to the lift platform 34 that sequentially interrupts a light beam in each of the interrupter modules as the blade ascends (or descends) with the lift piston 32, thus generating a signal 94 that is representative of the vertical height of the lift platform 34. Referring now to FIG. 4, there is illustrated a partial side view showing a series of the U shaped opto-interrupters 101 mounted on the post 102. As shown in FIG. 4, a blade 103 attached to the lift platform 34 is positioned to pass thru the open space in the U of the interrupters 101, thus breaking a light beam traversing the U portion, and triggering signal 94 at each interrupter as the lift platform 34 moves up or down with the lift piston.

A signal 90 indicates a home position for the lift platform 34 for the start of a test, and is responsive to an opto-interrupter module positioned about two inches above the dart hammer 20. A signal 92 indicates a bottom position for the lift platform 34 such that in this position of the lift platform 34 the drop piston 36 can contact the underside of dart pin 14 while the dart is resting on the dart hammer 20.

EXAMPLE

To illustrate an example operation of the drop test apparatus illustrated in FIG. 2 the following steps, which include only one of many possible sequencing operations for the set of electropneumatic piston type actuators, are performed with the aid of a computer preprogrammed to output control signals to lift and drop a dart weight from a desired height and record results.

1. Manually loading a dart weight 12 into the drop-tube 16 to contact the dart hammer 20, and entering a desired drop height in the computer memory.
2. Lifting the dart weight to a home position by extending the stem of drop piston 36 responsive to activating computer control signal 64, and activating the lift piston 32 to lift the dart.
3. Halting the lift piston 32 by contacting the stem of the home/start piston 72 at its home position, thus preventing further upward movement of the dart.
4. Extending the stem of safety piston 84 to insure that the lift platform 34 cannot drop to the bottom of the lift piston 32.
5. Manually loading a fresh sample of material 22 over the hole (not illustrated in FIG. 2) on the base plate 11.
6. Initiate lifting of the dart in drop-tube 16 by retracting the home/start piston 72 to its start position, and monitoring signal 94 in the computer to determine the height of the dart as it ascends in the drop-tube.
7. Comparing in the computer the height of the dart determined in step 6 with the desired drop height at activation of each opto-interrupt 101.
8. Dropping the dart when the height determined by signal 94 equals the desired drop height by retracting the stem of the drop piston 36.
9. Lowering the lift platform 34 via the lift piston 32, and halting the lift platform at its bottom position.
10. Raising the dart off the dart hammer 20 by extending the stem of drop piston 36 to contact the underside of drop pin 14, activating the lift piston 32 to raise the dart, and halting the lift platform at its home position.
11. Manually removing the spent sample 22 from the base plate 11, and examining the spent sample for cracks.
12. Manually entering the sample break classification (i.e. pass or fail) into a blank space provided on a computer data sheet display, and repeating the test procedure until 20 drops on successive fresh samples have been made according to ASTM-3029 specifications.

The operator has no other duties than to enter a minimum amount of data into the computer 100, load a selected dart in the drop-tube 16, load fresh sample specimens on the base plate 11, remove spent sample specimens, and record pass/fail results of each drop in a computer display. Accordingly, the operator is not concerned with lifting the dart or observing the drop height because those tasks are automated.

COMPUTER PROGRAM

For automating certain tasks in a test procedure for drop-weight testing according to this invention, it is only necessary to program a suitable computer with a routine that aids an operator in performing tasks according to an ASTM approved test procedure. A number of commercially available digital computer programs have been developed that can operate in a real time environment for reading in values of external variables and transmitting control signals to external devices, and that further facilitate console data entry, real time calculations, and displays. One such program, which is well known is "Microsoft Excel for Windows" which runs e.g., on any IBM® compatible machine with an 80386 processor or higher. This program, which has capacity to execute visual/basic commands, is particularly effective for automating repeated tasks and is the preferred program for use in this invention.

In a first step in testing a sample material, the computer 100 is programmed to aid the operator in selecting a dart weight and drop height for use as a starting dart weight and drop height in a more complicated test. This routine, which is illustrated in FIG. 3(a), aids the operator in by lifting dart weights for making successive drops using various trial dart weights that are dropped from various trial drop heights in order to select the lowest weight and lowest height that achieves a break in the sample material.

Figure 3A:
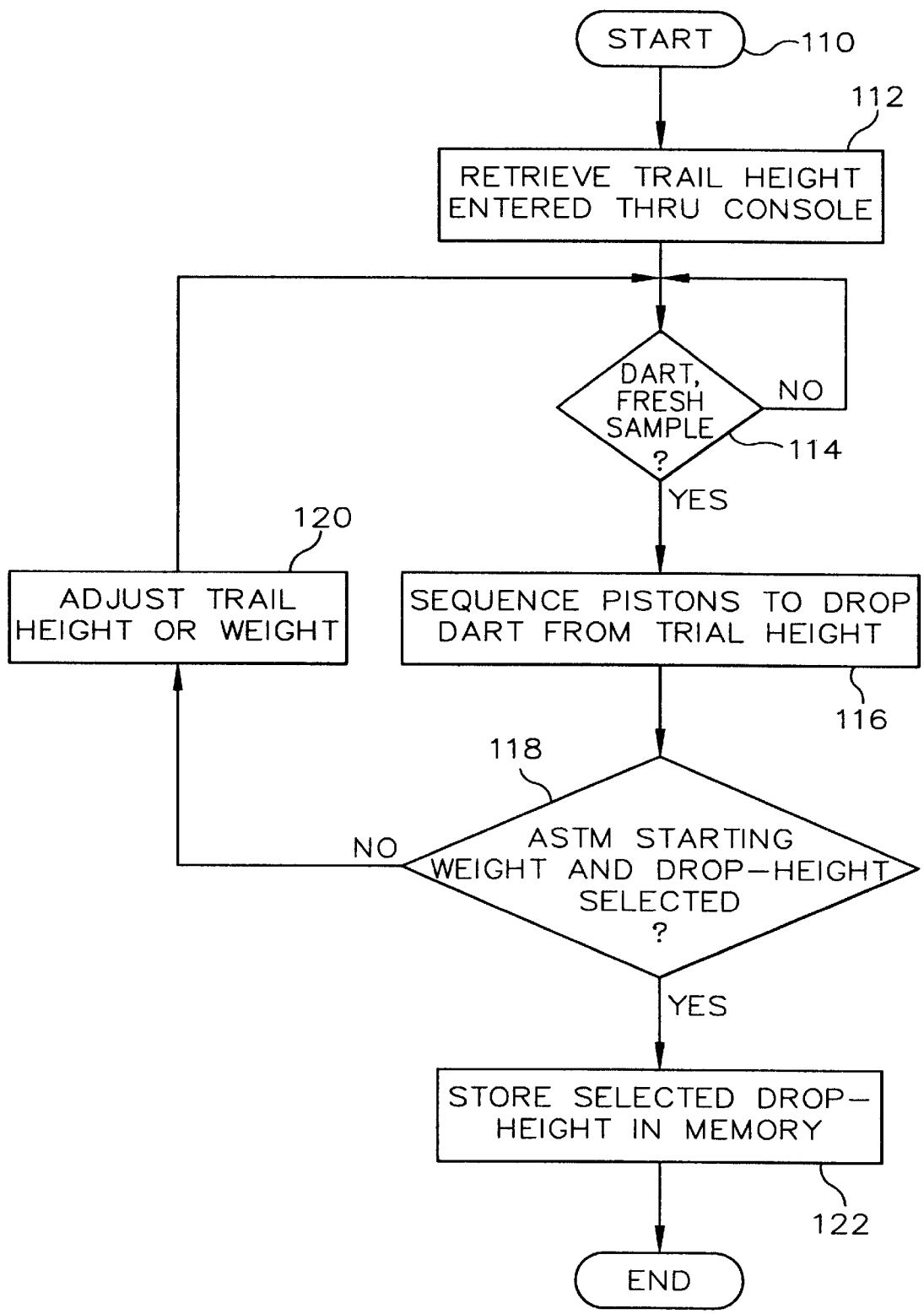
FIG. 3(a) is a simplified computer program flow chart illustrating a procedure for selecting a starting dart weight and drop height.

Referring specifically now to FIG. 3(a), the program for selecting a starting dart weight and a starting drop height is rendered operative at a start step 110 when initiated by an operator. Upon initiation the program scans and retrieves a first trial height from data entered through the console. This function step is illustrated at 112. Having the drop height information available, the program reaches decision block 114 as to whether or not a dart and fresh sample have been manually loaded by the operator. In effect this block 114 delays execution of the next step until the operator has completed the manual steps of loading the trial dart weight and sample material. When the manual steps are completed, the programmed actuator sequence operations are carried out as indicated in block 116. Sequencing of the electropneumatic actuators begins from one of two positions designated as the home position and the bottom position. Both of these positions have an associated opto-interrupt signal that is scanned by the program to verify the position. In the start position: the stem of drop piston 36 is extended to contact the underside of dart pin 14, the stem of safety piston 84 is extended to prevent lowering of the lift platform 34 to the bottom of the lift piston 32; air pressure is supplied to the inlet conduit 40 of lift piston 32 via switch 54 and a vent is applied to inlet 42 of lift piston 32 so that the lift piston 32 is urged upward. The stem of home/start piston 72, however, is extended to contact the top edge of lift platform 34 (i.e. home position), thus preventing upward movement of the lift piston 32 from the home position. The drop-weight test is initiated by retracting the stem of home/start piston 72 (i.e. start position) which allows upward movement of the lift piston with the attached dart weight. On reaching the predefined drop height, the stem of the drop piston 36 is retracted, thus releasing the dart 12 to impact the hammer 20. The switches 54 and 56 are reversed to lower the platform to the bottom position.

From the bottom position the drop piston 36 is extended to contact the underside of the dart pin 14, switches 54 and 56 again are reversed to raise the dart with the lift piston. On reaching the home position, the stem of the home/start piston 72 contacts the upper edge of lift platform 34 to prevent further upward movement of the lift piston 32. Next the decision block 118 is reached as to whether or not the starting dart weight and drop height for the more complicated test have been selected. If not, the trial weight and drop height are adjusted as indicated in block 120 and the process is repeated until a starting dart weight and starting dart height have been selected and stored in memory, as indicated in block 122.

Figure 3B:
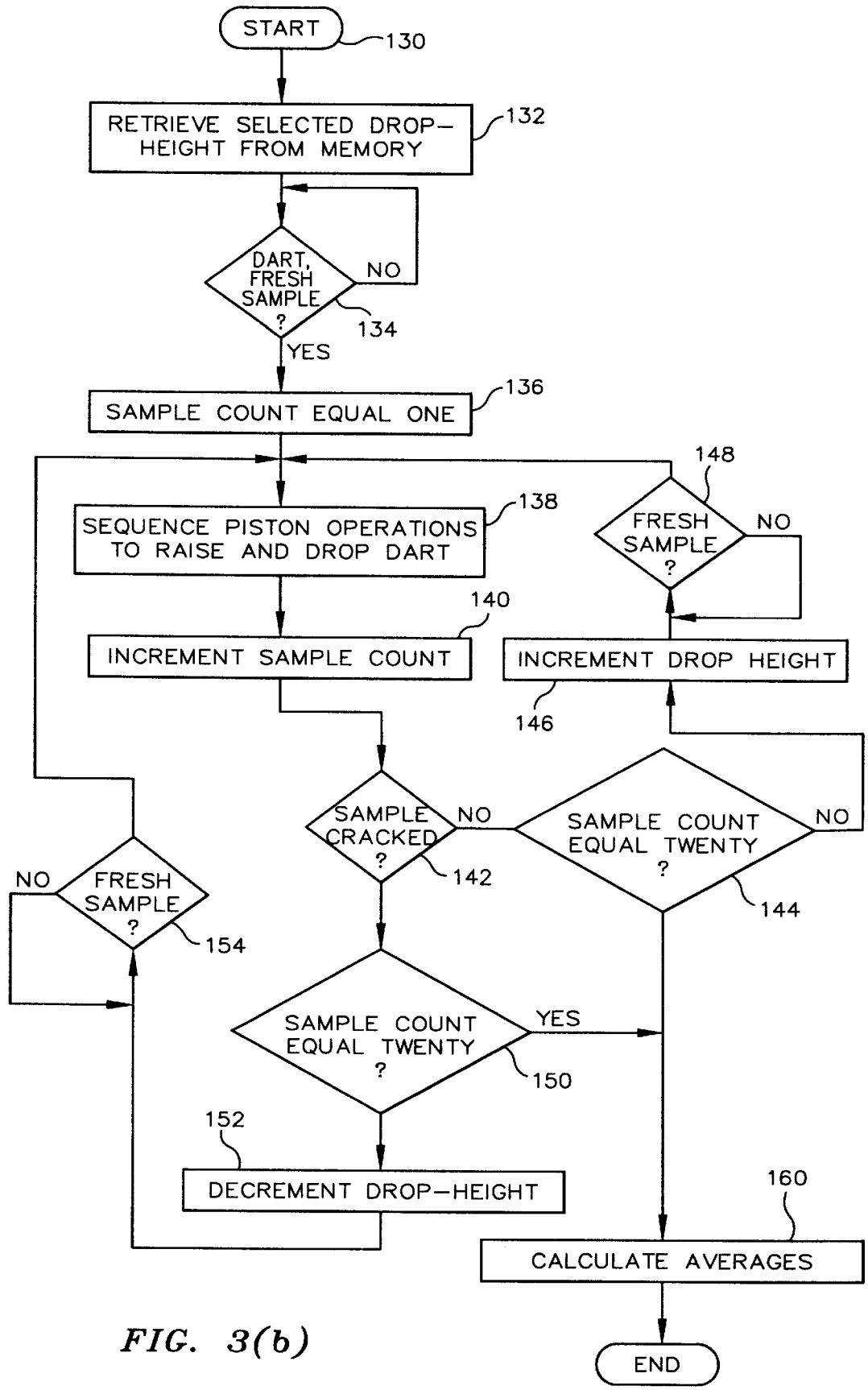
FIG. 3(b) is a simplified computer program flow chart illustrating the ASTM testing method according to this invention.

Referring now specifically to FIG. 3(b), the program for testing a series of twenty fresh samples according to an ASTM specification is rendered operative at a start step 130, when initiated by an operator. Upon initiation the program scans data entered into the program from the test procedure of FIG. 3(a), and retrieves the starting dart weight and starting drop height as indicated in block 132. Having this information available the program reaches decision block 134 as to whether or not the starting dart weight and fresh sample have been manually loaded. In effect decision block 134 delays execution of the next program step until the operator has completed the manual loading steps. When the manual loading steps are completed the program proceeds to block 136 where a sample counter is set to a value of one. The program then proceeds to block 138 where the electropneumatic pistons are sequenced in the same manner as described hereinabove with reference to block 116 in FIG. 3(a), with the lift piston remaining in the home position until block 138 is reentered. In the next step illustrated in block 140 the sample counter in incremented by a count of one. Proceeding next to decision block 142, the program is again paused to allow the operator to inspect the sample and manually enter the break classification of passed or failed into a blank provided on a computer display. If the sample is not cracked the program branches to decision block 144 as to whether or not twenty fresh samples have been tested. If not the program advances to block 146 where the drop height is incremented by one inch. Again the program is paused at block 148 for a fresh sample to be loaded by the operator. The program then reenters block 138 for repeating the sequence of piston operations. If the sample was not cracked in the drop-weight test, the program proceeds from block 142 to decision block 150 as to whether or not twenty fresh samples have tested. If not the program proceed to block 152 where the drop height is decremented by one inch. Again the program is paused at block 154 until a fresh sample material has been loaded by the operator. The program then reenters block 138 for repeating the sequence of piston operations. When the sample count equals twenty the program proceeds from either decision block 144 or 150 to calculation block 160 where mean failure height and impact stress are calculated. These calculated averages along with other results such as the number of failed samples can be provided in a printed report as illustrated in FIG. 5

While the invention has been described in terms of the presently preferred embodiment, reasonable variations and modifications are possible by those skilled in the art and such modifications and variations are within the scope of the described invention and the appended claims.

That which is claimed is:

1. Apparatus for drop-weight testing of a representative sample of a material that fails by cracking or shattering under a single blow delivering sufficient impact stress, said apparatus comprising:

(a) a test fixture comprising:
   i) a base plate having a hole;
   ii) at least one impact weight in the shape of a dart, and herein designated as a dart, having a lifting pin extending outwardly therefrom;
   iii) a drop-tube having a slot, wherein said drop-tube is vertically mounted above said hole in said base plate for slidably receiving said dart, wherein said dart can be raised in said drop-tube by positioning said lifting pin through said slot and using said lifting pin to lift said dart;

(b) a pneumatically powered lift means for lifting said dart, said lift means including a set of pneumatic pistons comprising:
   i) a drop piston having a retracted position and an extended position, said extended position being adapted for contacting the underside of said lifting pin;
   ii) a lift piston vertically mounted on a stationary frame, said lift piston being of pressure balance construction and having a relatively long stroke compared to said drop piston, wherein said lift piston is adapted for carrying said drop piston;
   iii) a home start piston mounted on said stationary frame at a home position, said home start piston having a retracted position and an extended position, said extended position being adapted for contacting said lift piston to prevent upward movement of said lift piston, and said retracted position being adapted for starting operation of said pneumatically powered lift mechanism; and
   (iv) a safety piston mounted on said stationary frame at a bottom position, said safety piston having a retracted position and an extended position, said extended position being adapted for stopping said lift piston;

said pneumatically powered lift means further including a set of electropneumatic actuators that are responsive to electronic signals for sequencing operation of said set of pneumatic pistons for contacting said lifting pin, then lifting and releasing said dart in said drop-tube;

(c) wherein said dart is released at a desired height in said drop-tube to free fall through said drop-tube and impact on said sample of material; and (d) means for generating a first signal representative of the position of said dart in said drop-tube.

2. A method for operating a drop-weight impact test apparatus for testing a number of representative samples of a material with the aid of a computer, wherein said material fails by cracking under sufficient impact stress delivered by a single blow, said method comprising:

(a) providing said computer with a data base of weight drop information including at least:
  (i) starting weight of a dart to be dropped through a drop-tube to impact said sample of material;
  (ii) a programmed starting height for releasing said dart;
  (iii) programmed number of fresh samples to be included in said impact test;

(b) activating a pneumatically powered mechanism for lifting said impact weight to be dropped responsive to a first signal;

(c) essentially constantly determining the height of said dart as it ascends in said drop-tube;

(d) repetitively comparing in said computer at frequent intervals, as said impact weight ascends in said drop-tube, the height of said impact weight in said drop-tube with said programmed height;

(e) releasing said dart when said comparison of step (d) indicates said programmed height has been attained;

(f) recording test results of said impact test as passed or failed to crack said sample, wherein said results are entered into a computer display;

(g) incrementing the previously programmed drop-height by one inch if said sample passed the crack test, and decrementing the previously programmed drop-height by one inch if said sample failed the crack test;

(h) operating steps (b) through (g) with a fresh sample until said number of representative of samples have been tested and (i) calculating an average failure height and impact stress for said number of representative samples.

3. A method in accordance with claim 2, additionally comprising:
  recording the results of said drop-weight impact test in said computer to provide a test report for multiple data items including:
    value of said impact weight;
    height at which said sample material failed;
    impact stress at failure;
    identification of sample material;
    number of failed samples; and
    total number of samples tested.

4. A method in accordance with claim 2, wherein said number of representative samples tested is twenty samples of materials selected from the group of materials consisting of polyethylene and polypropylene.

5. Apparatus in accordance with claim 1, wherein said drop-piston is mounted on a small platform designated herein as a lift platform, and wherein said means for generating a first signal representative of the position of said dart in said drop-tube comprises:
  a sensor post positioned along side of said lift piston;
  a plurality of spaced apart optoelectronic semiconductor modules mounted on said sensor post; and
  a blade attached to said lift platform for interrupting a light beam in said optoelectronic modules as said blade moves with said lift piston, wherein the interruption of said light beam generates a digital type electronic signal.

6. Apparatus in accordance with claim 5, wherein said plurality of optoelectronic modules mounted on said sensor post are spaced apart by a distance of about one inch.

* * * * *